US007025983B2

(12) United States Patent
Leung et al.

(10) Patent No.: US 7,025,983 B2
(45) Date of Patent: Apr. 11, 2006

(54) FAST DISSOLVING ORALLY CONSUMABLE FILMS

(75) Inventors: Sau-Hung Spence Leung, Parsippany, NJ (US); Robert S. Leone, Fanwood, NJ (US); Lori D. Kumar, Skillman, NJ (US); Neema Kulkarni, Randolph, NJ (US); Albert F. Sorg, Columbia, NJ (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 09/836,474

(22) Filed: Apr. 18, 2001

(65) Prior Publication Data

US 2001/0022964 A1 Sep. 20, 2001

Related U.S. Application Data

(62) Division of application No. 09/395,104, filed on Sep. 14, 1999, now Pat. No. 6,596,298.

(60) Provisional application No. 60/101,798, filed on Sep. 25, 1998.

(51) Int. Cl.
*A61F 13/00* (2006.01)
*A61K 9/00* (2006.01)

(52) U.S. Cl. .................. 424/435; 424/400; 424/434

(58) Field of Classification Search ............... 424/402, 424/404, 434, 435, 447, 448, 449, 400
See application file for complete search history.

(56) References Cited

U.S. PATENT DOCUMENTS

| | | | |
|---|---|---|---|
| 3,444,858 A | 5/1969 | Russell | |
| 3,803,300 A | 4/1974 | Pospischil et al. | ............ 424/28 |
| 4,197,289 A | 4/1980 | Sturzenegger et al. | |
| 4,562,020 A * | 12/1985 | Hijiya et al. | .................. 264/39 |
| 4,623,394 A | 11/1986 | Nakamura et al. | |
| 4,820,506 A | 4/1989 | Kleinberg et al. | ............. 426/3 |
| 4,925,670 A | 5/1990 | Schmidt | |
| 4,927,636 A | 5/1990 | Hijiya et al. | |
| 5,023,082 A | 6/1991 | Friedman et al. | ........... 424/426 |
| 5,047,244 A | 9/1991 | Sanvordeker et al. | |
| 5,284,659 A | 2/1994 | Cherukuri et al. | .......... 424/441 |
| 5,354,551 A | 10/1994 | Schmidt | |
| 5,411,945 A | 5/1995 | Ozaki et al. | |
| 5,456,745 A * | 10/1995 | Roreger et al. | ............. 106/128 |
| 5,518,902 A | 5/1996 | Ozaki et al. | |

(Continued)

FOREIGN PATENT DOCUMENTS

CA 1313620 2/1993

(Continued)

OTHER PUBLICATIONS

Shih, Frederick F., "Edible films from rice protein concentrate and pullulan", Cereal Chemistry, vol. 73, No. 3, 1966, pp. 406-409.

*Primary Examiner*—Thurman K. Page
*Assistant Examiner*—Humera N. Sheikh
(74) *Attorney, Agent, or Firm*—Darryl C. Little; Evan J. Federman

(57) ABSTRACT

Physiologically acceptable films, including edible films, are disclosed. The films include a water soluble film-forming polymer such as pullulan. Edible films are disclosed that include pullulan and antimicrobially effective amounts of the essential oils thymol, methyl salicylate, eucalyptol and menthol. The edible films are effective at killing the plaque-producing germs that cause dental plaque, gingivitis and bad breath. The film can also contain pharmaceutically active agents. Methods for producing the films are also disclosed.

11 Claims, 2 Drawing Sheets

U.S. PATENT DOCUMENTS

| | | | | |
|---|---|---|---|---|
| 5,629,003 A | * | 5/1997 | Horstmann et al. | 424/401 |
| 5,700,478 A | | 12/1997 | Biegajski et al. | 424/434 |
| 5,741,510 A | | 4/1998 | Rolf et al. | 424/448 |
| 5,948,430 A | * | 9/1999 | Zerbe et al. | 424/435 |

FOREIGN PATENT DOCUMENTS

| | | |
|---|---|---|
| EP | 0161681 | 11/1985 |
| EP | 0256611 | 2/1988 |
| EP | 0471558 | 2/1992 |
| EP | 0750905 | 1/1997 |
| EP | 0781546 | 2/1997 |
| EP | 0803243 | 10/1997 |
| JP | 62072609 | 4/1987 |
| JP | 62135417 | 6/1987 |
| JP | 63059855 | 3/1988 |
| JP | 63250318 | 10/1988 |
| JP | 63250319 | 10/1988 |
| JP | 63280014 | 11/1988 |
| JP | 63296655 | 12/1988 |
| JP | 63310817 | 12/1988 |
| JP | 63310818 | 12/1988 |
| JP | 04321619 | 11/1992 |
| JP | 5001198 | 1/1993 |
| JP | 541602 | 6/1993 |
| JP | 5236885 | 9/1993 |
| JP | 101790451 | 12/1996 |
| JP | 2642354 | 5/1997 |
| JP | 9124512 | 5/1997 |
| WO | 9303649 | 3/1993 |
| WO | 9731621 | 9/1997 |
| WO | 9811867 | 3/1998 |
| WO | WO-98/11867 * | 3/1998 |
| WO | 9820862 | 5/1998 |
| WO | 9826763 | 6/1998 |
| WO | 9826780 | 6/1998 |
| WO | 9855079 | 12/1998 |
| WO | 9917753 | 4/1999 |

\* cited by examiner

FAST DISSOLVING ORALLY CONSUMABLE FILMS

REFERENCE TO RELATED APPLICATIONS

This is a divisional of U.S. patent application Ser. No. 09/395,104, filed Sep. 14, 1999 now U.S. Pat. No. 6,596,298, which claims the benefit of U.S. provisional patent application No. 60/101,798, filed Sep. 25, 1998.

FIELD OF THE INVENTION

This invention relates to fast dissolving orally consumable films. The films are used to deliver breath deodorizing agents, antimicrobial agents and salivary stimulants to the oral cavity. The films can also be used to deliver pharmaceutically active agents.

BACKGROUND OF THE INVENTION

In a more perfect world, people would thoroughly cleanse their mouths after each meal as part of their routine oral hygienic practices. Unfortunately, several factors conspire to prevent widespread compliance with this basic requirement of a good oral cleaning regimen.

Oral cleansing can be difficult or inconvenient at times, depending on the nature of the cleansing and the situation in which the cleansing must occur. Brushing, flossing, cleaning your tongue and gargling using a variety of devices and compositions well-suited for the privacy of one's home are common oral care practices. However, the devices and compositions used in oral cleansing practices are less convenient to use away from home, where bathroom facilities might be scarce, unavailable or unsanitary.

As brushing, flossing, cleaning your tongue and gargling in public are not considered to be socially acceptable behaviors in many, if not all cultures, a variety of less obtrusive oral cleansing products have been developed. These include breath-freshening gums and lozenges. Although gums and lozenges have bee formulated to achieve a variety of beneficial effects, they are not always socially acceptable. For example, gum is expressly banned from certain institutions, such as schools as well as in certain countries, such as Singapore. Gums and mints are used over extended periods of time, and they require an amount of sucking or chewing action on the part of the consumer, which can be distracting, tedious and undesirable.

Another portable oral cleansing product is a mouthspray. Like a mouthwash, a mouthspray can provide the consumer with a quick burst of strong breath-freshening action, which might be overwhelming in an extended-consumption product like gum or lozenges. On the other hand, mouthsprays are obtrusive. Spraying a mouthspray typically generates a noise, which undesirably draws the attention of the public to the consumer. Moreover, mouthsprays are typically packaged in relatively expensive and complex metal canisters, which can clog in use and are not environmentally friendly. Furthermore, misdirecting the spray not only wastes the product, but can result in irritated eyes, a sticky face and/or stained clothing.

It has been proposed to use an edible film as a vehicle for unobtrusively delivering breath-freshening agents. See JP 5-236885. This Japanese patent application does not, however, teach the inclusion of antimicrobial agents in the film, using the film to decrease the amount of undesirable bacteria within the oral cavity, or stimulating saliva. Furthermore, this patent application does not disclose employing its film for purposes other than breath freshening or within cavities other than the mouth.

U.S. Pat. No. 5,518,902 to Ozaki et al. (Hayashibara) discloses high pullulan content products, such as edible films, dentifrices and pharmaceuticals (column 3, lines 44–56 and Example B-8). The products can include a variety of ingredients in addition to pullulan, such as other polysaccharides, polyhydric alcohols, antiseptics and flavor-imparting agents (column 4, line 58 to column 5, line 11). None of the essential oils, such as thymol, eucalyptol, methyl salicylate or menthol, are mentioned as suitable ingredients.

U.S. Pat. No. 5,411,945 to Ozaki et al. (Hayashibara) discloses a pullulan binder and products produced therewith, including edible films (Example B-2). The products can include a variety of ingredients in addition to pullulan, such as other polysaccharides, antibacterial agents, flavor-imparting agents and pharmaceutically active substances (column 4, lines 5–15). None of the essential oils are mentioned as suitable ingredients.

U.S. Pat. No. 4,851,394 to Kubodera discloses glucomannan/polyhydric alcohol edible films, which can comprise pullulan (column 3, line 59 to column 4, line 21). The films are contrasted with existing pullulan-based films, which are said to lack resistance to water (column 1 lines 40–44). None of the essential oils are mentioned as suitable ingredients.

U.S. Pat. No. 3,784,390 Hijiya et al. discloses pullulan films and their use in coating and packing materials for foods, pharmaceuticals and other oxygen sensitive materials. All of the examples in this patent teach mixing pullulan in hot water.

U.S. Pat. No. 4,623,394 Nakamura et al. discloses a gradually disintegrable molded article that can be a film made with pullulan. The articles contain a particular heteromannan, which can be locust bean gum.

U.S. Pat. No. 4,562,020 Hijiya et al. discloses a process for producing a self-supporting film of a glucan, which can be pullulan.

Japanese Patent Document JP5-1198 discloses films made of polyvinyl alcohol and at least one of carrageenan, water-soluble cellulose alpha-starch and water-soluble polysaccharides.

WO 99/17753 discloses rapidly dissolving films for delivery of drugs to be adsorbed in the digestive tract.

WO 98/26780 discloses a flat, foil, paper or wafer type presentation for the application and release of active substances in the buccal cavity. The specific active ingredient disclosed in WO 98/26780 is buprenorphine.

WO 98/20862 discloses a film for use in the oral cavity that can contain a cosmetic or pharmaceutical active substance.

WO 98/26763 discloses a flat, foil, paper or wafer like presentation for release of active substances into the buccal cavity. The particular active disclosed is apomorphine.

Despite the existence of rapidly dissolving orally consumable films in the prior art, there is still room for improvement in such films, and in processes for making them.

All references cited herein are incorporated herein by reference in their entireties.

SUMMARY OF THE INVENTION

The invention provides a physiologically acceptable film, which is particularly well adapted to adhere to and rapidly dissolve in the mouth of a consumer. In a first embodiment of the invention, the film delivers at least one oral care agent, such as antimicrobial agents and salivary stimulants. The antimicrobial agents are effective against germs that cause halitosis, dental plaque, and gingivitis. The salivary stimulants are effective against the condition known as xerostomia or dry mouth. Additionally, the oral care films are a breath freshener effective against oral malodor. The film former used to make the films according to the present invention entraps the oral care agents in the oral cavity to provide extended efficacy.

In a second embodiment of the invention, the rapidly dissolvable film acts as a vehicle for administering a pharmaceutically active agent orally, through a mucous membrane or an open wound of a patient.

The invention is also directed to a method for producing a supple, non-self-adhering film especially suitable for oral delivery. The method comprises mixing a film forming agent and at least one stabilizing agent to provide a film-forming mixture; dissolving water-soluble ingredients in water to provide an aqueous solution; combining the film-forming mixture and the aqueous solution to provide a hydrated polymer gel; mixing oils to form an oil mixture; adding the oil mixture to the hydrated polymer gel and mixing to provide a uniform emulsified gel; casting the uniform gel on a substrate; and drying the cast gel to provide a film.

DETAILED DESCRIPTION OF PREFERRED EMBODIMENTS

Description of Oral Care Film Compositions

Figure 1:
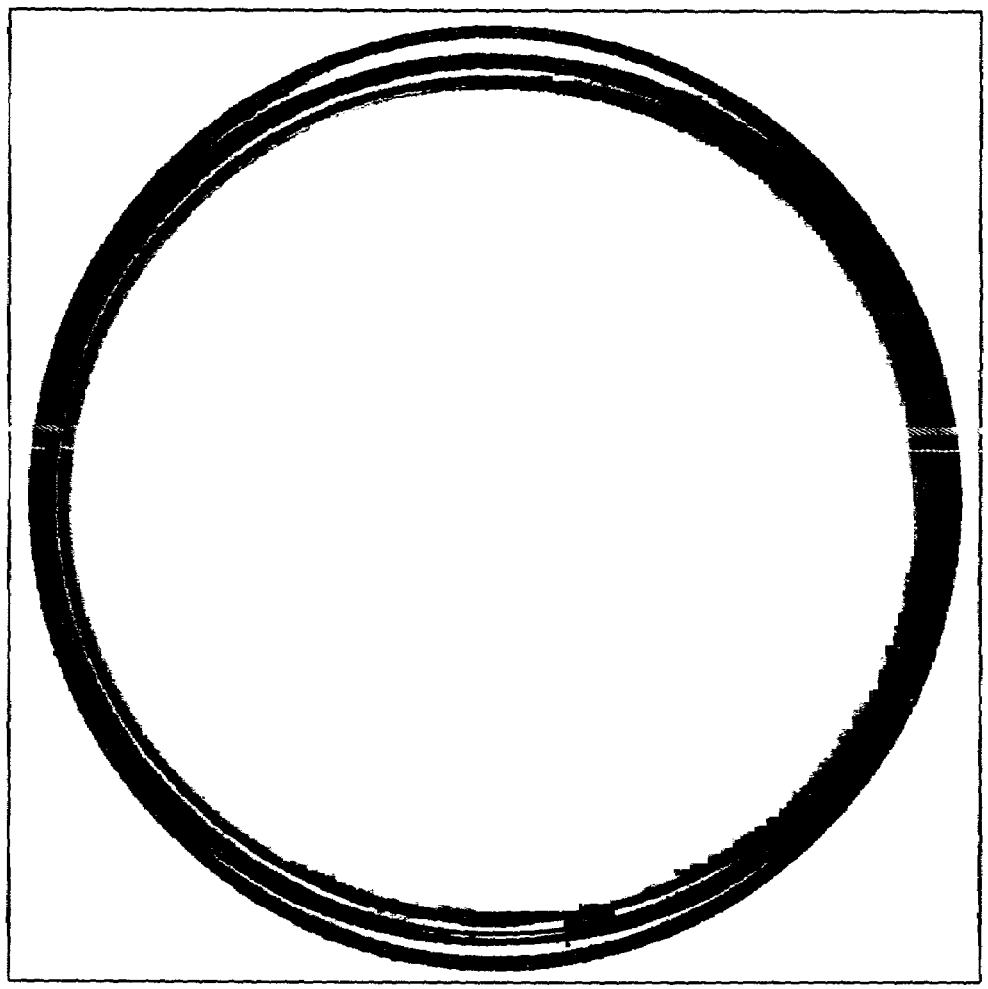
FIG. 1 is a photograph of an agar plate spread with *Streptococcus mutans*, ATCC 25175, and exposed to a film according to the present invention that contains 0.391 mg of essential oils.

The first embodiment of the invention is a physiologically acceptable film that is particularly well adapted to adhere to and dissolve in a mouth of a consumer to deliver an antimicrobial agent that kills germs that cause halitosis, dental plaque and gingivitis. Thus, the film can be an effective tool in the prevention and treatment of halitosis, dental plaque accumulation, dental tartar accumulation and gingivitis. This film preferably comprises pullulan, thymol, methyl salicylate, eucalyptol and menthol.

LISTERINE® brand mouthwash is, perhaps, the most well-known example of an antiseptic oral composition that has proven effective in killing microbes in the oral cavity that are responsible for plaque, gingivitis and bad breath. LISTERINE® brand mouthwash achieves its antimicrobial effect through a combination of essential oils that penetrate and kill the microorganisms. These essential oils include precisely balanced amounts of thymol, methyl salicylate, menthol and eucalypidl (hereinafter "the essential oils") in a hydro alcoholic solution. Many bad breath bacteria live in pits or fissure on the surface of the tongue. Listerine® Antiseptic mouthwash reduces bad breath because of high concentrations of antimicrobial agents in a liquid medium that can easily penetrate into these pits and fissures. This would not be possible with a solid dosage form containing low amounts of these antimicrobial ingredients. However, the preferred consumable film of the invention captures a significant portion of the hygienic benefits and the consumer appeal of LISTERINE® brand mouthwash, in a more portable and unobtrusively consumed form.

It was a significant challenge to maintain the essential oil interaction and relatively high oil content of LISTERINE® brand mouthwash in a film. However, the inventors have overcome this challenge in providing the film of the invention.

A further aspect of this invention is that while the amounts of LISTERINE® essential oils are relatively high for incorporation in a film, the film according to the present invention still delivers a lower total amount of essential oils per unit dose when compared to that of LISTERINE® mouthwash. Yet the film suprisingly provides antimicrobial efficacy in the oral cavity. The inventors theorize that the preferred film forming ingredient, pullulan, forms a thin layer on the oral surfaces entrapping the small amount of essential oils which are capable of penetrating into the pits and fissures of the oral cavity to provide sustained antimicrobial efficacy.

Although the inventors are presently unaware of any other breath-freshening consumable film that provides antimicrobial efficacy, they are aware of a consumable film disclosed in JP 5-236885, which is said to possess breath-freshening activity, but is not described as possessing any ingredients having significant antimicrobial activity. Moreover, JP 5-236885 teaches that its film should contain flavor and extract in amounts of 5 to 7 wt %, with the flavor being added as an oil (the essential oils are not disclosed), whereas the film of the invention preferably has an oil content of at least about 10 wt %, more preferably about 15 wt % to about 30 wt %, most preferably about 15 wt % to about 25 wt %. Except as otherwise noted in the examples, the amounts of oils and other ingredients in the film are wt % after the film formulation has been dried to create the film.

The amounts of the specific essential oils used in the film compositions can vary as long as they are in amounts sufficient to provide antimicrobial efficacy. Generally the amount of thymol, methyl salicylate and eucalyptol is from about 0.01 to about 4 wt % of the film composition, preferably about 0.50 to about 3.0 wt % and even more preferably from about 0.70 to about 2.0 wt % of the film. Menthol can be added from about 0.01 to about 15 wt % of the composition, preferably about 2.0 to about 10 wt % and even more preferably from about 3 to about 9 wt % of the film. The amounts added can be readily determined to those skilled in the art and can exceed these amounts as long as the total oil content does not create sticking or other processing problems. In certain embodiments, the essential oils are combined in amounts synergistically effective to kill the plaque-producing germs that cause dental plaque, gingivitis and bad breath.

A major difficulty in formulating a film having such a relatively high oil content is that simply increasing the amount of oil in the film without determining the precise proportions of the many other ingredients typically results in a film that is too moist and therefore difficult to handle or process. The inventors have discovered how to provide a high oil content film that is moist enough so that it is not brittle, but is not so moist that it feels undesirably slimy or significantly adheres to adjacent films. Thus, a non-self-adhering film according to the invention can be stored in contact with another such film (e.g., in a stack), or can be wound about itself (e.g., around a spool), without having to place a non-stick agent (e.g., a plastic film, paper or other support) between adjacent portions of film.

The film-forming agent used in the films according to the present invention can be selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. A preferred film former is pullulan, in amounts ranging from about 0.01 to about 99 wt %, preferably about 30 to about 80 wt %, more preferably from about 45 to about 70 wt % of the film and even more preferably from about 60 to about 65 wt % of the film.

The film of the invention preferably comprises pullulan as a film-forming agent and the essential oils as antimicrobial/flavoring agents, and can further comprise water, additional antimicrobial agents, additional film-forming agents, plasticizing agents, additional flavoring agents, sulfur precipitating agents, saliva stimulating agents, cooling agents, surfactants, stabilizing agents, emulsifying agents, thickening agents, binding agents, coloring agents, sweeteners, fragrances, and the like.

Due to the relatively high oil content in the oral care film, it is preferable to avoid substantial amounts of humectant in the film (and more preferable to have no humectant in the film), so as to avoid producing an overly moist, self-adhering film. In particular, it is preferred to formulate the film with a plasticizing agent other than glycerin, which is also a humectant, and with a sweetener other than sorbitol, which is a mild humectant.

Sulfur precipitating agents that reduce oral malodor can also be added to the oral care films according to the present invention. These agents bind with, and inactivate, the volatile sulfur compounds that cause a large percentage of oral malodor. Sulfur precipitating agents useful in the present invention include metal salts such as copper salts and zinc salts. Preferred salts include copper gluconate, zinc citrate and zinc gluconate. The amount of sulfur precipitating agent is from about 0.01 to about 2 wt %, preferably about 0.15 wt % to about 1.5 wt %, even more preferably about 0.25 wt % to about 1.0 wt % of the film.

Saliva stimulating agents can also be added to the oral care films according to the present invention. Useful saliva stimulating agents are those disclosed in U.S. Pat. No. 4,820,506, which is incorporated by reference herein in its entirety. Saliva stimulating agents include food acids such as citric, lactic, malic, succinic, ascorbic, adipic, fumaric and tartaric acids. Preferred food acids are citric, malic and ascorbic acids. The amount of saliva stimulating agents in the film is from about 0.01 to about 12 wt %, preferably about 1 wt % to about 10 wt %, even more preferably about 2.5 wt % to about 6 wt %.

Preferred plasticizing agents include triacetin in amounts ranging from about 0 to about 20 wt %, preferably about 0 to about 2 wt %. Other suitable plasticizing agents include monoacetin and diacetin.

Preferred cooling agents include monomenthyl succinate, in amounts ranging from about 0.001 to about 2.0 wt %, preferably about 0.2 to about 0.4 wt %. A monomenthyl succinate containing cooling agent is available from Mane, Inc. Other suitable cooling agents include WS3, WS23, Ultracool II and the like.

Preferred surfactants include mono and diglycerides of fatty acids and polyoxyethylene sorbitol esters, such as, Atmos 300 and Polysorbate 80. The surfactant can be added in amounts ranging from about 0.5 to about 15 wt %, preferably about 1 to about 5 wt % of the film. Other suitable surfactants include pluronic acid, sodium lauryl sulfate, and the like.

Preferred stabilizing agents include xanthan gum, locust bean gum and carrageenan, in amounts ranging from about 0 to about 10 wt %, preferably about 0.1 to about 2 wt % of the film. Other suitable stabilizing agents include guar gum and the like.

Preferred emulsifying agents include triethanolamine stearate, quaternary ammonium compounds, acacia, gelatin, lecithin, bentonite, veegum, and the like, in amounts ranging from about 0 to about 5 wt %, preferably about 0.01 to about 0.7 wt % of the film.

Preferred thickening agents include methylcellulose, carboxyl methylcellulose, and the like, in amounts ranging from about 0 to about 20 wt %, preferably about 0.01 to about 5 wt %.

Preferred binding agents include starch, in amounts ranging from about 0 to about 10 wt %, preferably about 0.01 to about 2 wt % of the film.

Suitable sweeteners that can be included are those well known in the art, including both natural and artificial sweeteners. Suitable sweeteners include, e.g.:

A. water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin;

B. water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like;

C. dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like;

D. water-soluble sweeteners derived from naturally occurring water-soluble sweeteners, such as a chlorinated derivative of ordinary sugar (sucrose), known, for example, under the product description of sucralose; and E. protein based sweeteners such as thaumatoccous danielli (Thaumatin I and II).

In general, an effective amount of auxiliary sweetener is utilized to provide the level of sweetness desired for a particular composition, and this amount will vary with the sweetener selected. This amount will normally be 0.01% to about 10% by weight of the composition when using an easily extractable sweetener. The water-soluble sweeteners described in category A above, are usually used in amounts of about 0.01 to about 10 wt %, and preferably in amounts of about 2 to about 5 wt %. Some of the sweeteners in category A (e.g., glycyrrhizin) can be used in amounts set forth for categories B–E below due to the sweeteners' known sweetening ability. In contrast, the sweeteners described in categories B–E are generally used in amounts of about 0.01 to about 10 wt %, with about 2 to about 8 wt % being preferred and about 3 to about 6 wt % being most preferred. These amounts may be used to achieve a desired level of sweetness independent from the flavor level achieved from any optional flavor oils used. Of course, sweeteners need not be added to films intended for non-oral administration.

The flavorings that can be used include those known to the skilled artisan, such as natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit and fruit essences including apple, pear, peach, strawberry, raspberry, cherry, plum, pineapple, apricot and so forth. These flavorings can be used individually or in admixture. Commonly used flavors include mints such as peppermint, artificial vanilla, cinnamon derivatives, and various fruit flavors, whether employed individually or in admixture. Flavorings such as aldehydes and esters including cinnamyl acetate, cinnamaldehyde, citral, diethylacetal, dihydrocarvyl acetate, eugenyl formate, p-methylanisole, and so forth may also be used. Generally, any flavoring or food additive, such as those described in Chemicals Used in Food Processing, publication 1274 by the National Academy of Sciences, pages 63–258, may be used. Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like.

The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. In general, amounts of about 0.1 to about 30 wt % are useable with amounts of about 2 to about 25 wt % being preferred and amounts from about 8 to about 10 wt % are more preferred.

The compositions of this invention can also contain coloring agents or colorants. The coloring agents are used in amounts effective to produce the desired color. The coloring agents useful in the present invention, include pigments such as titanium dioxide, which may be incorporated in amounts of up to about 5 wt %, and preferably less than about 1 wt %. Colorants can also include natural food colors and dyes suitable for food, drug and cosmetic applications. These colorants are known as FD&C dyes and lakes. The materials acceptable for the foregoing spectrum of use are preferably water-soluble, and include FD&C Blue No. 2, which is the disodium salt of 5,5-indigotindisulfonic acid. Similarly, the dye known as Green No. 3 comprises a triphenylmethane dye and is the monosodium salt of 4-[4-N-ethyl-p-sulfobenzylamino) diphenyl-methylene]-[1-N-ethyl-N-p-sulfonium benzyl)-2,5-cyclo-hexadienimine]. A full recitation of all FD&C and D&C dyes and their corresponding chemical structures may be found in the Kirk-Othmer Encyclopedia of Chemical Technology, Volume 5, Pages 857–884, which text is accordingly incorporated herein by reference.

Antimicrobial Efficacy of Oral Care Films

The preferred embodiment of the oral care film composition according to the present invention contains the essential oils used in Listerine(mouthwash to provide antimicrobial efficacy. The films are shaped and sized to be placed in the oral cavity. The film adheres to a surface in the mouth, usually the roof of the mouth or the tongue, and quickly dissolves. The amount of essential oils in one individual film that is a preferred size for placing in the mouth is significantly lower than that in the recommended amount, 20 ml, of Listerine® mouthwash.

In a preferred formula according to the present invention, the amount of thymol and eucalyptol in the film is about 70 times less than in the mouthwash. The amount of methyl salicylate in the film is about 46 times less than in the mouthwash. The amount of menthol in the film is about 2.8 times less than in the mouthwash. These figures are based on comparing a 20 ml dose of liquid mouthwash with a 0.0358 gram film.

The inventors have unexpectedly found that the film provides sustained antimicrobial efficacy at these low amounts of oils. The inventors believe that the efficacy of the essential oils is enhanced by the creation of a layer of pullulan in the oral cavity that holds the essential oils. This is unexpected because pullulan is water-soluble and the film dissolves very quickly.

The extended antimicrobial activity is shown in the following experiments.

The purpose of these experiments was to determine the antibacterial efficacy of an application of a breath film on tongue malodor microorganisms thirty, sixty or ninety minutes after use. The thirty minute study also tested the efficacy of using two films. Subjects' baseline oral malodor microbial recoverable counts were determined by plating the microorganisms recovered from a tongue swab on a selective agar medium. The test product was dispensed and subjects dissolved one or two breath films on their tongue. Subjects remained on the premises and returned for a second tongue swab thirty, sixty or ninety minutes after placement of the test product on their tongue. After a forty-eight hour washout period, subjects returned for a no treatment control.

The thirty minute single film use group showed a reduction in mean log malodor microbial counts compared to the control group. The data was borderline statistically significant ($p=0.052$). The difference between the one film group and the no treatment control group represented a 42.7% reduction in malodor microbial colony counts.

Statistically significant malodor microbial reduction was also observed with the two film use group. A 79.6% reduction in malodor microbial colony counts was obtained ($p<0.001$).

Statistically significant malodor microbial reduction was observed sixty minutes after use of a single breath film. A 69.8% reduction in malodor microbial colony counts was obtained ($p=0.002$).

Significant malodor reduction was also observed ninety minutes after use of a single breath film. A 69.1% reduction in malodor microbial colony counts was obtained p=0.006).

The data from these studies support the following conclusions: (1) Pullulan polymer-based breath film containing essential oils is an effective antibacterial composition against oral malodor causing bacteria and (2) significant in vivo bacterial reductions were achieved at thirty, sixty and ninety minutes post use.

Experimental Procedures

The procedures used in these antimicrobial studies were as follows. The subject were required to refrain from all oral hygiene procedures (e.g., toothbrushing, oral lavage) eating or drinking any food, beverage or confectionery products from midnight prior to the study and until the study was completed on each test day. Subjects refrained from smoking on mornings prior to the odor evaluations.

In vivo Germ Kill Assay

1. Materials

Test tubes containing 10 ml of sterile 0.01% peptone

Sterile Swabs

OOPS III Agar (B.-F. Turng, G. E. Minah, and W. A. Falkler. Development of an Agar Medium for Detection of Oral $H_2S$-producing Organisms. J Dent Res 76 IADR Abstracts 1997.):

| | | |
|---|---|---|
| Columbia Agar Base (Catalogue #DF0792-17-3) | 44 | grams |
| Distilled Water | 1 | liter |
| Lead Acetate[a] (Sigma L3396) | 0.2 | grams |
| Hemin Solution[b] (Sigma H-1652) | 2 | ml |
| Glutathione[c] (Sigma G4251) | 1.2 | grams |

Forty-four grams of Columbia Blood Agar Base was suspended in 1 liter distilled water and boiled to dissolve completely. The media was sterilized at 121–124° C. for 15 minutes.
[a]Dissolved 0.2 grams of lead acetate in 1 ml of distilled $H_2O$ and filter sterilized. Added after autoclaving the base media.
[b]Dissolved 50 mg of hemin in 1 ml of 1N NaOH; qs'd to 100 ml with distilled $H_2O$. Filter sterilized. Added 2 ml per liter of OOPS III after autoclaving base media.
[c]Dissolved 1.2 grams of glutathione in 10 ml of distilled $H_2O$. Filter sterilized. Added after autoclaving base media.

2. Procedure a. All media were prereduced in an anaerobic chamber overnight. Plates were loosely wrapped in plastic bags to prevent excessive drying.

b. Panelists refrained from oral hygiene, eating and drinking from midnight prior to the assay and until the assay was complete. Twelve panelists were used for the sixty and ninety minute experiments. Eighteen panelists were used for the thirty minute experiments.

c. Each panelist swabbed the right side of his tongue by placing the swab at the midpoint of the tongue and swiping forward to the tip. The swab was placed in a tube of peptone.

d. The panelist received a film treatment, either a single or double film. Panelists placed the breath film on the left side of their tongue covering the tongue from the midpoint to the tip and allowed the film to dissolve with the mouth slightly open for thirty seconds to prevent the film from sticking to the palate.

e. After thirty or sixty minutes, panelists swabbed the left side of the tongue by placing the swab at the midpoint of the tongue and swiping forward to the tip. The swab was placed in a tube of peptone.

f. The tubes of peptone were vortexed vigorously for 10 seconds, and serial dilutions were made. The $10^{-4}$ dilution was plated in duplicate on OOPS III Agar using a Spiral Biotech Autoplate 4000 (Bethesda, Md.). All plates were identified with the subject's initials, assay date, sampling time station, and replicate number.

g. The plates were incubated in an anaerobic chamber at 35–37° C. for 7 days to permit full development of colonies without overgrowth.

h. After a 48 hour wash out period, panelists returned for the no treatment control. No film was applied, and steps (e) through (g) were followed as described above.

i. After a 48 hour wash out period, the sixty minute panelists returned for another single film application. Steps (a) through (h) were followed, with the exception that panelists returned after 90 min in step e.

j. The dark-pigmented colonies ($H_2S$-producing organisms) were counted as whole plate counts by hand under appropriate magnification or by Segment counts using a Spiral Biotech counting template. The appropriate code was entered on the data sheet to permit interpretation of the counts. The CFU's counted were converted to CFU/ml by dividing by the appropriate exponential volume constant listed in Table A and multiplying by 1000. This value was then multiplied by the dilution factor of the plate ($10^4$).

TABLE A

Exponential Volume Constants for Segment Pairs

| Last Counted Segment | Exponential Volume Constant |
|---|---|
| 8 | 1.214 |
| 9 | 2.968 |
| 10 | 5.500 |
| 11 | 9.157 |
| 12 | 14.482 |
| 13 | 25.015 |
| Total Plate | 50.030 |

The film used in the in vivo germ kill tests was Example 19 as described in Table 2. The films used in the study were approximately 22 mm×32 mm, between about 0.0013 and 0.0015 inches thick and weighed between about 35 to about 37 mg.

Figure 2:
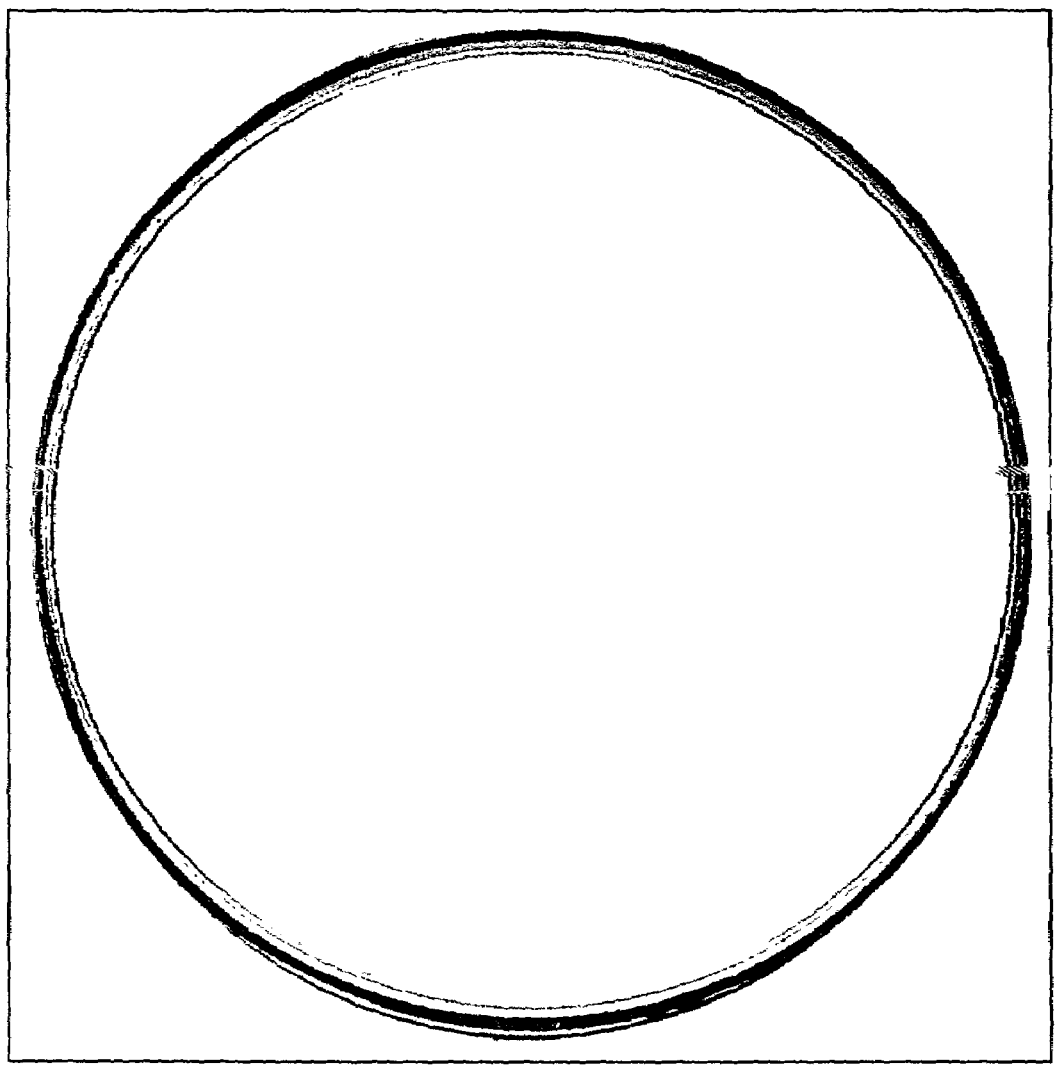
FIG. 2 is a photograph of an agar plate spread with *Streptococcus mutans*, ATCC 25175, and exposed to drops of an essential oil mixture containing 0.391 mg of essential oils per drop.

The enhanced activity of the essential oil containing pullulan film is also shown in FIGS. 1 and 2. FIG. 1 is a photograph of an agar plate spread with *Streptococcus mutans*, ATCC # 25175, to which a piece of an essential oil pullulan film according to the present invention was added. The piece of film delivered approximately 0.391 mg of essential oils using Example 15 listed below.

FIG. 2 is a photograph of an agar plate spread with *Streptococcus mutans*, ATCC # 25175 to which drops of essential oils have been added. The drops were 148 ul in volume and contained 0.391 mg of essential oils. The percentages of each essential oil in the drop are 2.200% menthol, 0.186% eucalyptol, 0.186% methyl salicylate and 0.1300% thymol in a hydro alcohol solution.

The area or zone of inhibition around the film in FIG. 1 is much larger than the dimensions of the film. This is due to the presence of pullulan because the oils in the pullulan film were spread by the pullulan, diffused outward and did not wash away after repeated rinses. In contrast, the essential oils in FIG. 2 did not diffuse away from the droplet, remained as a circle and easily washed off after 1–2 rinses. This shows that the antimicrobial efficacy of the essential oils is enhanced by the presence of pullulan.

Methods for Preparing Essential Oil Containing Films

Methods for preparing films according to the invention are capable of encapsulating the oil ingredients within the film-forming matrix and maintaining the integrity of the film, even when the film contains oils in amounts of 10 wt % or more.

In certain methods for preparing films according to the invention, the film-forming ingredients are mixed and hydrated with water separately from the water-soluble ingredients, which are mixed in aqueous solution separately from the organic ingredients and surfactants. In these methods, the final formulation is preferably produced by mixing the film-forming phase with the aqueous phase, then mixing in the organic phase, which includes surfactants, such as Polysorbate 80 and Atmos 300. This mass is mixed until emulsified. In other embodiments, the aqueous and film forming phases are combined into a single phase by dissolving the water soluble ingredients in the water and then adding the gums to hydrate. The organic phase is then added to this single aqueous phase.

The resulting formulation is cast on a suitable substrate and dried to form a film. The film is preferably air-dried or dried under warm air and cut to a desired dimension, packaged and stored. The film can contain from about 0.1% to about 10 wt % moisture, preferably from about 3% to about 8 wt % moisture, even more preferably from about 4 to about 7 wt % moisture.

The film-forming phase can include pullulan and stabilizing agents such as xanthan gum, locust bean gum and carrageenan. These ingredients are mixed and then hydrated in water for about 30 to about 48 hours to form a gel. The water is preferably heated to a temperature of about 25 to about 45° C. to promote hydration. The amount of water is about 40 to 80% of the gel. The resulting hydrated gel is then chilled to a temperature of about 20 to about 30° C. for about 1 to about 48 hours. The water is preferably deionized.

The aqueous phase can include ingredients such as coloring agent(s), copper gluconate and sweetener. The water is preferably deionized and the amount of water used is about 5 to about 80 wt % of the final gel mixture.

If sodium saccharin and copper gluconate are both ingredients in the formulation, it is preferable to dissolve them separately in solution to avoid precipitation.

In a preferred method of producing essential oil containing films according to the invention, it is possible to hydrate the film-forming ingredients and combine all of the ingredients without heating. The preferred method of producing films comprises dissolving the water-soluble ingredients in water to form an aqueous mixture; mixing the film-forming ingredients in powder form to form a powder mixture; adding the powder mixture to the aqueous mixture to form a hydrated polymer gel; stirring the hydrated polymer at room temperature for about 30 minutes to about 48 hours; mixing the cooling agent, thymol and menthol in the flavor oil to form an oil mixture; adding methyl salicylate; eucalyptol and surfactants to the oil mixture; adding the oil mixture to the hydrated polymer gel and mixing until uniform; deaerating the film until air bubbles are removed, casting the uniform mixture on a suitable substrate; and drying the cast mixture to form a film.

The preferred method for making an essential oil containing film hydrates the film-forming ingredients without heating the water. Heating the ingredients increases energy costs in the manufacturing process. Moreover, heating results in undesirable losses of volatile ingredients to evaporation, which also affects the germ killing activity of the composition due to the loss of essential oils. Further, mixing the oils in two steps minimizes the amount of flavor lost.

While not wishing to be bound by any theories, it is believed that the film-forming ingredients can be hydrated and mixed without heating due to an ionic effect known as the Donnan equilibrium. Hydrating the film-forming agents in the presence of electrolytes in solution effectively lowers the viscosity of the polymer gel being formed, thus increasing the efficiency of the hydrating process. The water-soluble ingredients of the formulation provide the electrolytes, which are dissolved in the hydration solution prior to addition of the film-forming ingredients. High-shear mixing also accelerates hydration, which delumps the powders, providing greater it surface area for water contact. In addition, local heating effects, generated in the shear regions, provide energy for hydration without substantially raising the temperature of the mass.

It is preferable to avoid adding both copper gluconate and saccharin at the same time to the aqueous solution, as a precipitate will form. Thus, it is preferred to combine sweeteners other than saccharin with copper gluconate.

Description of Film Compositions that Deliver Pharmaceutical Agents

A second embodiment of the invention is a fast dissolving film that includes at least one physiologically acceptable, pharmaceutically active agent. The expression "physiologically acceptable" as used herein is intended to encompass compounds, which upon administration to a patient, are adequately tolerated without causing undue negative side effects. The expression encompasses edible compounds.

The expression "pharmaceutically active agents" as used herein is intended to encompass agents other than foods, which promote a structural and/or functional change in and/or on bodies to which they have been administered. These agents are not particularly limited; however, they should be physiologically acceptable and compatible with the film. Suitable pharmaceutically active agents include, but are not limited to:

A. antimicrobial agents, such as triclosan, cetyl pyridium chloride, domiphen bromide, quaternary ammonium salts, zinc compounds, sanguinarine, fluorides, alexidine, octonidine, EDTA, and the like, B. non-steroidal anti-inflammatory drugs, such as aspirin, acetaminophen, ibuprofen, ketoprofen, diflunisal, fenoprofen calcium, naproxen, tolmetin sodium, indomethacin, and the like, C. anti-tussives, such as benzonatate, caramiphen edisylate, menthol, dextromethorphan hydrobromide, chlophedianol hydrochloride, and the like, D. decongestants, such as pseudoephedrine hydrochloride, phenylpherine, phenylpropanolamine, pseudoephedrine sulfate, and the like, E. anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like, F. expectorants, such as guaifenesin, ipecac, potassium iodide, terpin hydrate, and the like, G. anti-diarrheals, such a loperamide, and the like, H. $H_2$-antagonists, such as famotidine, ranitidine, and the like; and I. proton pump inhibitors, such as omeprazole, lansoprazole, and the like,
J. general nonselective CNS depressants, such as aliphatic alcohols, barbiturates and the like,
K. general nonselective CNS stimulants such as caffeine, nicotine, strychnine, picrotoxin, pentylenetetrazol and the like,
L. drugs that selectively modify CNS function such as phenyhydantoin, phenobarbital, primidone, carbamazepine, ethosukimide, methsuximide, phensuximide, trimethadione, diazepam, benzodiazepines, phenacemide, pheneturide, acetazolamide, sulthiame, bromide, and the like,
M. antiparkinsonism drugs such as levodopa, amantadine and the like,
N. narcotic-analgesics such as morphine, heroin, hydromorphone, metopon, oxymorphone, levorphanol, codeine, hydrocodone, xycodone, nalorphine, naloxone, naltrexone and the like,
O. analgesic-antipyretics such as salycilates, phenylbutazone, indomethacin, phenacetin and the like,
P. psychopharmacological drugs such as chlorpromazine, methotrimeprazine, haloperidol, clozapine, reserpine, imipramine, tranylcypromine, phenelzine, lithium and the like.

The amount of medicament that can be used in the rapidly dissolving films, according to the present invention, is dependent upon the dose needed to provide an effective amount of the medicament. Examples of doses for specific medicaments that can be delivered per one strip of rapidly dissolving oral film are reviewed in Table 1.

TABLE 1

| MEDICAMENT | DOSE |
| --- | --- |
| Chlorpheniramine Maleate | 4 mg. |
| Brompheniramine Maleate | 4 mg. |
| Dexchlorpheniramine | 2 mg. |
| Dexbrompheniramine | 2 mg. |
| Triprolidine Hydrochloride | 2.5 mg. |
| Acrivastine | 8 mg. |
| Azatadine Maleate | 1 mg. |
| Loratidine | 10 mg. |
| Phenylephrine Hydrochloride | 10 mg. |
| Dextromethorphan Hydrochloride | 10–20 mg. |
| Ketoprofen | 12.5 mg. |
| Sumatriptan Succinate | 35–70 mg. |
| Zolmitriptan | 2.5 mg. |
| Loperamide | 2 mg. |
| Famotidine | 10 mg. |
| Nicotine | 2 mg. |
| Diphenhydramine Hydrochloride | 25 mg. |
| Pseudoephedrine Hydrochloride | 30 mg. |

The ingredients used to make the pharmaceutical containing films are similar to those used to make oral care films. Specifically, the plasticizing agents, cooling agents, surfactants, stabilizing agents, emulsifiers, thickening agents, binding agents, film formers, sweeteners, flavors and colors described above can also be used in all of the films according to the present invention.

The films that deliver a pharmaceutical agent can also include a triglyceride. Examples of triglycerides include vegetable oils such as corn oil, sunflower oil, peanut oil, olive oil, canola oil, soybean oil and mixtures thereof. A preferred triglyceride is olive oil. The triglyceride is added to the film in amounts from about 0.1 wt % to 16 about 12 wt %, preferably in a range from about 0.5 wt % to about 9 wt %, of the film.

The films that contain pharmaceutical agents also can include a preservative. The preservative is added in amounts from about 0.001 wt % to about 5 wt %, preferably from about 0.01 wt % to about 1 wt % of the film. Preferred preservatives include sodium benzoate and potassium sorbate.

The pharmaceutical agent containing films can also include a polyethylene oxide compound. The molecular weight of the polyethylene oxide compound ranges from about 50,000 to about 6,000,000. A preferred polyethylene oxide compound is N-10 available from Union Carbide Corporation. The polyethylene oxide compound is added in amounts from about 0.1 wt % to about 5 wt %, preferably from about 0.2 wt 20% to about 4.0 wt % of the film.

The pharmaceutical agent containing films can also include propylene glycol. The propylene glycol is added in amounts from about 1 wt % to about 20 wt %, preferably from about 5 wt % to about 15 wt % of the film.

The active ingredient used in the film can be coated to mask the taste of the active ingredient or to prevent the active ingredient from numbing the tongue or other surfaces in the oral cavity. The coatings that can be used are known to those skilled in the art. These include polymers such, as Eudragit®, cellulosics, such as ethylcellulose, and the like.

An additional way to mask the taste of the active ingredient is by using an ion exchange resin such as Amberlite RP-69, available from Rohm and Haas, and Dow XYS-40010.00, available from the Dow Chemcial Co.

EXAMPLES

The invention will be illustrated in more detail with reference to the following Examples, but it should be understood that the present invention is not deemed to be limited thereto.

Preparation Method I

The following method was used to prepare the films of Examples 1–13.

A. The film-forming ingredients (e.g., xanthan gum, locust bean gum, carrageenan and pullulan) other than Polysorbate 80 and Atmos 300 are mixed and hydrated in hot purified water to form a gel and stored in a refrigerator overnight at a temperature of approximately 4° C. to form preparation A.
B. The coloring agent(s), copper gluconate and sweetener are added to and dissolved in purified water to form preparation B.
C. Preparation B is added to preparation A and mixed well to form preparation C.
D. The flavoring agent and the oils (e.g., cooling agent, thymol, methyl salicylate, eucalyptol and menthol) are mixed to form preparation D.
E. The polysorbate 80 and Atmos 300 are added to preparation D and mixed well to form preparation E.
F. Preparation E is added to preparation C and mixed well to form preparation F.

Preparation F is poured on a mold and cast to form a film of a desired thickness at room temperature. The film is dried under warm air and cut to a desired dimension, packaged and stored.

Preparation Method II

Examples 14–18 were prepared using a preferred method, which comprised the following steps:

A. dissolve copper gluconate, acesulfame K, aspartame, glycerin, sorbitol and dye in purified water to form an aqueous mixture;

B. mix pullulan, xanthan gum, locust bean gum and carrageenan together in powder form to form a powder mixture;
C. add the powder mixture from step B to the aqueous mixture from step A to form a hydrated polymer gel;
D. stir the hydrated polymer from step C at slow speed (about 50–100 RPM) overnight at room temperature;
E. mix and dissolve cooling agent, thymol and menthol in the flavor oil;
F. add methyl salicylate, eucalyptol, Polysorbate 80 and Atmos 300 to the oil mixture from step E;
G. add the oil mixture from step F to the hydrated polymer gel from step D and mix until uniform;
H. cast the uniform mixture from step G on a suitable backing; and
I. dry the cast mixture to form a film.

Example 1

Example 1 produced a film according to the invention having a blue-green tint, a mint odor and a refreshing mint taste.

Examples 2–4

Examples 2–4 contain sorbitol, glycerin or both. These examples yielded products that easily broke off pieces, or were too moist and/or self-adhering. However they did produce films that rapidly dissolved in the oral cavity with a refreshing mint taste.

Examples 5–6

Examples 5 and 6 removed glycerin and sorbitol. The resultant films did not stick together during processing and packaging and were more moisture stable over a long time frame.

Examples 7–9

Examples 7–9 were produced to determine the effect of Avicel® on germ killing activity. While Examples 7–9 produced more acceptable films from a processing and handling perspective, they had diminished antimicrobial activity relative to films without Avicel®, such as Example 8.

Examples 10–15

Examples 10–15 varied the amounts of aspartame and menthol to alter the sweetness and coolness of the film.

Example 16

Example 16 was prepared by replacing the sorbitol replaced with maltitol, which has less humectant properties. The resultant film was less sticky during processing and long term storage.

Example 17

Example 17 is prepared in which pullulan is replaced with another film former, polyvinyl pyrrolidone, to produce films according to the invention.

Example 18

Example 18 is prepared in which pullulan is partially replaced with another film former, konjac gum, to produce films according to the invention.

Example 19

Example 19 represents a film containing a salivary stimulant, citric acid.

Example 20

Example 20 is the film composition used in the antimicrobial efficacy studies described above.

The formulas for examples 1–20 are summarized in Table 2. The amounts in these examples are presented as the actual weight (grams) or w/w %. These formulas create the solution/gel that is cast and dried into a film. The actual amount of each ingredient in the finished, dried film depends upon the amount of relative moisture removed during drying.

TABLE 2

| Ingredient | Ex. 1 w/w % | 2 wt (g) | 3 wt (g) | 4 wt (g) | 5 wt (g) | 6 wt (g) | 7 wt (g) | 8 wt (g) | 9 wt (g) |
|---|---|---|---|---|---|---|---|---|---|
| Xanthan Gum, Food Grade | 0.1070 | | | | | | 11.60 | 12.60 | 11.60 |
| Xanthan Gum 1% solution | | 3.85 | 3.85 | 3.85 | 3.85 | 3.85 | | | |
| Locust Bean Gum, Clarified | 0.2150 | | | | | | 23.40 | 25.40 | 23.40 |
| Locust Bean Gum (1% solution) | | 7.70 | 7.70 | 7.70 | 7.70 | 7.70 | | | |
| Polyvinyl Pyrrolidone | | | | | | | | | |
| Konjac Gum | | | | | | | | | |
| Carrageenan | 1.0730 | | | | | | 116.60 | 126.10 | 116.60 |
| Carrageenan (5% solution) | | 7.70 | 7.70 | 7.70 | 7.70 | 7.70 | | | |
| Avicel | | | | | | | 500.00 | | 500.00 |
| Pullulan | 51.5780 | | | | | | 5604.00 | 6513.00 | 5949.00 |
| Pullulan (25% sol) | | 74 | 74 | 74 | 74 | 74 | | | |
| Thymol NF | 0.4070 | 0.146 | | | 0.146 | 0.146 | 40.70 | 40.70 | 40.70 |
| Methyl Salicylate NF | 0.4210 | 0.151 | | | 0.151 | 0.151 | 58.50 | 58.50 | 58.50 |
| Eucalyptol | 0.5850 | 0.21 | | | 0.21 | 0.21 | 42.10 | 42.10 | 42.10 |
| Menthol USP | 5.8830 | 2.23 | | | 2.11 | 2.11 | 588.00 | 588.00 | 588.00 |

TABLE 2-continued

| Ingredient | | | | | | | | | |
|---|---|---|---|---|---|---|---|---|---|
| Mint flavor | 8.3640 | 2 | | | 3.0 | 3.0 | 836.00 | 836.00 | 836.00 |
| Citric Acid | | | | | | | | | |
| Copper gluconate | 1.1150 | 0.275 | | | 0.41 | 0.14 | 112.00 | 112.00 | 112.00 |
| Purified water, USP/EP | 22.32 | 2 | 10.22 | 12.22 | 8.0 | 8.0 | 2230.00 | 2230.00 | 2230.00 |
| Sod. saccharin USP granulate | 6.6910 | 1.8 | 1.4 | 1.4 | 2.0 | 2.4 | | | |
| Sodium saccharin | | | | | | | 609.00 | 609.00 | 609.00 |
| Acesulfame-K | | | | | | | | | |
| Aspartame | | | | | | | | | |
| Cooling agent | | 0.05 | | | 0.05 | 0.05 | 13.90 | 13.90 | 13.90 |
| Maltitol | | | | | | | | | |
| Sorbitol (crystalline) | | | | | | | 64.30 | 64.30 | 64.30 |
| Sorbitol 70% sol. | | 4 | 4.0 | | | | | | |
| Glycerin | | 2 | | 2.0 | | | 136.00 | 136.00 | 136.00 |
| Polysorbate 80 NF/EP | 0.5580 | 0.3 | 0.2 | 0.2 | 0.2 | 0.2 | 112.00 | 112.00 | 112.00 |
| Atmos 300 | 0.5580 | | | | | | 112.00 | 112.00 | 112.00 |
| Atlas 3000 | | 0.3 | 0.2 | 0.2 | 0.2 | 0.2 | | | |
| Hi Set C Starch | | | | | | | | | 77.0 |
| FD&C Green #3 | 0.0084 | 0.3 | 0.3 | 0.3 | 0.3 | 0.3 | 0.84 | 0.84 | 0.84 |
| D&C Yellow #10 | | | | | | | | | |

| Ingredient | 10 wt (g) | 11 wt (g) | 12 wt (g) | 13 wt (g) | 14 w/w % | 15 w/w % | 16 w/w % | 17 w/w % | 18 w/w % | 19 w/w % | 20 w/w % |
|---|---|---|---|---|---|---|---|---|---|---|---|
| Xanthan Gum, Food Grade | 0.0385 | 0.0385 | 0.0385 | 0.0385 | 0.0342 | 0.0342 | 0.0342 | 0.04 | 0.04 | 0.34 | 0.0342 |
| Xanthan Gum (1% solution) | | | | | | | | | | | |
| Locust Bean Gum, Clarified | 0.077 | 0.077 | 0.077 | 0.077 | 0.0684 | 0.0684 | 0.0684 | 0.07 | 0.07 | 0.68 | 0.0684 |
| Locust Bean Gum (1% solution) | | | | | | | | | | | |
| Polyvinyl Pyrrolidone | | | | | | | | 16.5 | | | |
| Konjac Gum | | | | | | | | | 5.0 | | |
| Carrageenan | 0.385 | 0.385 | 0.385 | 0.385 | 0.342 | 0.342 | 0.342 | 0.34 | 0.34 | .34 | 0.342 |
| Carrageenan (5% solution) | | | | | | | | | | | |
| Avicel | | | | | | | | | | | |
| Pullulan | 18.5 | 18.5 | 18.5 | 18.5 | 16.43 | 16.43 | 16.43 | | 11.0 | 16.34 | 16.43 |
| Pullulan (25% sol) | | | | | | | | | | | |
| Thymol NF | 0.146 | 0.146 | 0.146 | 0.146 | 0.130 | 0.13 | 0.13 | 0.13 | 0.13 | 0.129 | 0.13 |
| Methyl Salicylate NF | 0.21 | 0.21 | 0.21 | 0.21 | 0.186 | 0.186 | 0.186 | 0.186 | 0.186 | 0.185 | 0.18 |
| Eucalyptol | 0.21 | 0.21 | 0.21 | 0.21 | 0.186 | 0.186 | 0.186 | 0.186 | 0.186 | 0.185 | 0.18 |
| Menthol USP | 2.11 | 1.95 | 2.36 | 2.33 | 2.096 | 2.520 | 2.096 | 2.096 | 2.096 | 2.084 | 2.096 |
| Mint flavor | 3.0 | 3.0 | 3.0 | 3.0 | 2.664 | 2.344 | 2.664 | 2.664 | 2.664 | 2.649 | 2.0 |
| Citric Acid | | | | | | | | | | | 2.5 |
| Copper gluconate | 0.4 | 0.4 | 0.4 | 0.4 | 0.355 | 0.355 | 0.355 | 0.35 | 0.35 | 0.353 | 0.355 |
| Purified water, USP/EP | 84.25 | 84.25 | 84.25 | 84.25 | 74.81 | 74.63 | 74.81 | 75 | 75 | 74.39 | 72.2168 |
| Sod. saccharin USP granulate | | | | | | | | | | | |
| Sodium saccharin | | | | | | | | | | | |
| Acesulfame-K | 0.5 | 0.5 | 0.5 | 0.5 | 0.444 | 0.444 | 0.444 | 0.45 | 0.45 | .04420 | 0.444 |
| Aspartame | 1.30 | 1.60 | 1.30 | 1.60 | 1.421 | 1.421 | 1.421 | 1.4 | 1.4 | 1.413 | 1.421 |
| Cooling agent | 0.10 | 0.10 | 0.10 | 0.10 | 0.089 | 0.089 | 0.089 | 0.089 | 0.089 | 0.088 | 0.89 |
| Maltitol | | | | | | | 2.80 | | | | |
| Sorbitol (crystalline) | | | | | | | | | | | |
| Sorbitol 70% sol. | | | | | | | | | | 0.199 | |
| Glycerin | | | | | | | | | | 0.418 | |
| Polysorbate 80 NF/EP | 0.4 | 0.4 | 0.4 | 0.4 | 0.355 | 0.355 | 0.355 | 0.355 | 0.355 | 0.353 | 0.355 |
| Atmos 300 | | | | | 0.355 | .0355 | 0.355 | 0.355 | 0.355 | 0.353 | 0.355 |
| Atlas 3000 | 0.4 | 0.4 | 0.4 | 0.4 | | | | | | | |
| Hi Set C Starch | | | | | | | | | | | |
| FD&C Green #3 | 0.003 | 0.003 | 0.003 | 0.003 | 0.0026 | 0.0026 | 0.0026 | 0.0026 | 0.0026 | | |
| D&C Yellow #10 | | | | | | | | | | | |

The following examples are films according to the second embodiment of the present invention, in which the rapidly dissolving film contains a pharmaceutical agent. Examples 21A–21E, listed in Table 3, are medicament containing rapidly dissolvable oral film formulas. The amounts in Table 3 are in milligrams.

TABLE 3

| Example Number | 21A | 21B | 21C | 21D | 21E |
|---|---|---|---|---|---|
| Dextromethorphan HBr | 7.500 | | | | |
| Phenylepherine HCI | | 10.0000 | 10.0000 | | |
| Chlorpheniramine Maleate | | | 4.0000 | | |
| Loperamide HCl | | | | 2.0000 | |
| Nicotine | | | | | 2.0000 |
| Xanthan Gum | 0.0818 | 0.0818 | 0.0818 | 0.0818 | 0.0818 |
| Locust Bean Gum | 0.0954 | 0.0954 | 0.0954 | 0.0954 | 0.0954 |
| Carrageenan | 0.4088 | 0.4088 | 0.4088 | 0.4088 | 0.4088 |
| Pullulan | 21.8036 | 21.8036 | 21.8036 | 21.8036 | 21.8036 |
| Sodium Benzoate | 0.0954 | 0.0954 | 0.0954 | 0.0954 | 0.0954 |
| Acesulfame Potassium Salt | 0.6814 | 0.6814 | 0.6814 | 0.6814 | 0.6814 |
| Aspartame NF | 1.9078 | 1.9078 | 1.9078 | 1.9078 | 1.9078 |
| Purified Water | * | * | * | * | * |
| Cooling agent | 0.1363 | 0.1363 | 0.1363 | 0.1363 | 0.1363 |
| Menthol | 2.7255 | 2.7255 | 2.7255 | 2.7255 | 2.7255 |
| Polysorbate 80 NF | 0.4770 | 0.4770 | 0.4770 | 0.4770 | 0.4770 |
| Atmos 300 | 0.4770 | 0.4770 | 0.4770 | 0.4770 | 0.4770 |
| Propylene Glycol | 4.0882 | 4.0882 | 4.0882 | 4.0882 | 4.0882 |
| Olive Oil | 0.6814 | 0.6814 | 0.6814 | 0.6814 | 0.6814 |
| Titanium Dioxide | 0.3407 | 0.3407 | 0.3407 | 0.3407 | 0.3407 |
| Total Dose Weight | 41.5000 | 44.0000 | 48.0000 | 36.0000 | 36.0000 |

*Calculated assuming complete evaporation of water from the films after drying

Table 4 summarizes additional films according to the present invention. The amounts in Table 4 are % w/w prior to drying.

TABLE 4

| | Examples | | | | | | | | |
|---|---|---|---|---|---|---|---|---|---|
| | 22A | 22B | 22C | 22D | 22E | 22F | 22G | 22H | 22I |
| Xanthan Gum | .03 | .03 | .06 | .03 | .03 | .03 | .06 | .06 | .06 |
| Locust Bean Gum | .07 | .07 | .07 | .07 | .07 | .07 | .07 | .07 | .07 |
| Carrageenan | 0.3 | 0.3 | 0.3 | 0.3 | 0.3 | 0.3 | 0.3 | 0.3 | 0.3 |
| Pullulan | 16.0 | 16.0 | 16.0 | 16.0 | 16.0 | 16.0 | 16.0 | 16.0 | 16.0 |
| Sodium Benzoate | 0.1 | 0.1 | 0.1 | .07 | .07 | .07 | .07 | .07 | .07 |
| Acesulfame Potassium | 0.5 | 0.5 | 0.5 | 0.5 | 0.5 | 0.5 | 0.5 | 0.5 | 0.5 |
| Aspartame | 1.4 | 1.4 | 1.4 | 1.4 | 1.4 | 1.4 | 1.4 | 1.4 | 1.4 |
| Water | qs100 | qs100 | qs100 | Qs100 | qs100 | qs100 | qs100 | qs100 | Qs100 |
| Cooling agent | 0.1 | 0.1 | 0.1 | 0.1 | 0.1 | 0.1 | 0.1 | 0.1 | 0.1 |
| Menthol | 2.0 | 2.0 | 2.0 | 1.3 | 2.0 | 2.0 | 2.0 | 2.0 | 2.0 |
| Polysorbate 80 | 0.35 | 0.35 | 0.35 | 0.35 | 0.35 | 0.35 | 0.35 | 0.35 | 0.35 |
| Atmos 300 | 0.35 | 0.35 | 0.35 | 0.35 | 0.35 | 0.35 | 0.35 | 0.35 | 0.35 |
| Propylene Glycol | 1.0 | 1.0 | 1.0 | 1.0 | 1.0 | 1.0 | 3.0 | 3.0 | 3.0 |
| Peg 1450 | — | 3.10 | — | — | — | — | — | — | — |
| Olive Oil | — | — | — | 1–2 | 2.0 | 2.0 | .5–2 | — | .5 |
| Polyox N-10 | — | — | — | — | — | — | — | — | 1.0 |
| Titanium Dioxide | — | 0.25 | 0.25 | 0.25 | 0.25 | — | 0.25 | — | 0.25 |

Example 22A was used to make films containing a) 7.5 mg of dextromethorphan hydrobromide, b) 2.5 mg of tripolidine, c) 4.0 mg of chlorpheniramine maleate and d) 12.5 mg of diphenhydramine hydrochloride.

Example 22B was used to make a film containing 10 mg of dextrometorphan hydrobromide.

Example 22C was used to make a film containing 10 mg of dextromethorphan hydrobromide.

Example 22D was used to make a film containing a) 10 mg of phenylepherine hydrochloride, b) 10 mg of phenylepherine hydrochloride and 4 mg of chlorpheniramine maleate and c) 10 mg of dextromethorphan hydrobromide.

Example 22E was used to make a film containing 7.5 mg dextromethorphan hydrobromide.

Example 22F was used to make a film containing 20 mg of coated dextromethorphan hydrobromide to provide a 7.5 mg dose.

Example 22G was used to make a film containing a) 7.5 mg dextromethorphan hydrobromide, b) 10 mg phenylepherine hydrochloride and c) 10 mg phenylepherine hydrochloride and 4 mg chlorpheniramine maleate.

Example 22H was used to make a film containing 15 mg of dextromethorphan hydrobromide.

Example 22I was used to make a film containing 15 mg of dextromethorphan hydrobromide.

Processes for Making Pharmecutical Containing Films

Example 22A was made using the following procedure.

1. Add the sodium benzoate and sweeteners to water.
2. Mix the locust bean gum, xanthan gum and carrageenan together.
3. Add the gum mixture to the mixture of step 1 and mix until dissolved.
4. Mix the active ingredient with either water or propylene glycol. Heat if needed.
5. Add the remaining ingredients to the mixture of step 4 or mix the remaining ingredients in a separate mixture.
6. Add the mixtures of step 4 and step 5 to the mixture of step 3. Cast and dry to make a film and cut to a size to achieve the desired dose.

Examples 22B–22E were made using the following procedure.

1. Add the sodium benzoate to water heated to 50 C. Mix to dissolve.

2. Separately, add the Peg 1450, titanium dioxide and active ingredient to the mixture of step 1, mixing with each addition.

3. Mix the locust bean gum, xanthan gum and carrageenan together.

4. Add the gums to the mixture of step 2 and mix until dissolve.

5. Add the remaining ingredients together with heat if needed.

6. Add the mixture of steps 4 and 5 together. Cast and dry to make a film and cut to a size to achieve the desired dose.

Examples 22F–22I were made in the same manner as Examples 20B–20E, except the active was dispersed right before the film was cast.

While the invention has been described in detail and with reference to specific examples thereof, it will be apparent to one skilled in the art that various changes and modifications can be made therein without departing from the spirit and scope thereof.

What is claimed is:

1. A method for preparing a physiologically compatible film, said method comprising:
   mixing water soluble polymer and at least one stabilizing agent selected from the group consisting of xanthan gum, locust bean gum, carrageenan, guar gum and mixtures thereof to provide a film-forming mixture;
   dissolving water-soluble ingredients in water to provide an electrolyte containing aqueous solution;
   combining said film-forming mixture and said aqueous solution to provide a hydrated polymer gel;
   mixing oils to form an oil mixture that comprises at least two essential oils selected from the group consisting of thymol, methyl salicylate, eucalyptol, and menthol wherein the total amount of said oils in said oil mixture is at least about 5 wt % of the total weight of ingredients;
   adding said oil mixture to said hydrated polymer gel and mixing to provide a uniform gel;
   casting the uniform gel on a substrate; and
   drying the cast gel to provide said film that adheres to and dissolves in a consumer's mouth.

2. The method according to claim 1, wherein at least one surfactant is mixed into said oil mixture.

3. The method according to claim 1, wherein said total amount of oils is at least about 15 wt %.

4. The method according to claim 1, wherein said drying is conducted until said film has a moisture content of about 3 wt % to about 8 wt %.

5. The method according to claim 1, wherein, prior to being combined with said aqueous solution, said film-forming mixture is hydrated with water at a temperature of about 25 to about 50° C. and subsequently chilled to a temperature of about 4 to about 30° C. for about 2 to 48 hours.

6. The method according to claim 1, wherein said film-forming mixture is a powder, which is directly combined with said aqueous solution.

7. The method according to claim 6, wherein said hydrated polymer gel is formed without heating.

8. The method according to claim 7, wherein said hydrated polymer gel is stirred at room temperature for about 2 to about 48 hours.

9. The method according to claim 8, wherein said oil mixture is prepared by mixing thymol and menthol in a flavor oil, and subsequently adding methyl salicylate and eucalyptol.

10. A non-self-adhering film produced according to the method of claim 1.

11. The method according to claim 1, wherein the water soluble film former is selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

* * * * *